(12) United States Patent
Kloepfer et al.

(10) Patent No.: US 6,696,240 B1
(45) Date of Patent: Feb. 24, 2004

(54) CAPILLARY TEST STRIP TO SEPARATE PARTICULATES

(75) Inventors: Hans G. Kloepfer, Noblesville, IN (US); Mary A. Kloepfer, Noblesville, IN (US); Charles W. Roach, Arcadia, IN (US); Reinhard Hafellner, Leoben (AT); Bernd Mlekusch, Veit an der Glan (AT)

(73) Assignee: Micronix, Inc., Carmel, IN (US)

( * ) Notice: Subject to any disclaimer, the term of this patent is extended or adjusted under 35 U.S.C. 154(b) by 0 days.

(21) Appl. No.: 09/696,156

(22) Filed: Oct. 25, 2000

Related U.S. Application Data
(60) Provisional application No. 60/161,500, filed on Oct. 26, 1999.

(51) Int. Cl.[7] .................................................. C12Q 1/00
(52) U.S. Cl. ............................ 435/4; 435/287.9; 422/56
(58) Field of Search .......................... 435/4, 14, 287.9, 435/805, 970; 422/55–58; 436/169, 170

(56) References Cited

U.S. PATENT DOCUMENTS

| | | | |
|---|---|---|---|
| 4,288,228 A | | 9/1981 | Oberhardt |
| 4,477,575 A | | 10/1984 | Vogel et al. |
| 4,761,381 A | * | 8/1988 | Blatt et al. ................... 436/165 |
| 4,774,192 A | | 9/1988 | Terminiello et al. |
| 4,790,979 A | * | 12/1988 | Terminiello et al. .......... 422/56 |
| 4,816,224 A | | 3/1989 | Vogel et al. |
| 4,883,764 A | | 11/1989 | Kloepfer |
| 4,900,424 A | | 2/1990 | Birth et al. |
| 4,987,085 A | | 1/1991 | Allen et al. |
| 5,019,351 A | | 5/1991 | Schulz |
| 5,039,617 A | | 8/1991 | McDonald et al. |
| 5,135,719 A | | 8/1992 | Hillman et al. |
| 5,139,685 A | | 8/1992 | de Castro et al. |
| 5,141,868 A | | 8/1992 | Shanks et al. |
| 5,144,139 A | | 9/1992 | Hillman et al. |
| 5,212,060 A | | 5/1993 | Maddox |
| 5,223,219 A | | 6/1993 | Subramanian et al. |
| 5,260,195 A | | 11/1993 | Azhar ........................ 435/25 |
| 5,262,067 A | | 11/1993 | Wilk et al. |
| 5,306,623 A | | 4/1994 | Kiser et al. |
| 5,418,142 A | | 5/1995 | Kiser et al. |
| 5,423,989 A | | 6/1995 | Allen et al. |
| 5,478,751 A | | 12/1995 | Oosta et al. |
| 5,536,470 A | | 7/1996 | Frey et al. |
| 5,597,463 A | | 1/1997 | Birch et al. |
| 5,658,444 A | | 8/1997 | Black et al. |
| 5,665,238 A | | 9/1997 | Whitson et al. |
| 5,766,552 A | | 6/1998 | Doshi et al. |
| 5,789,255 A | | 8/1998 | Yu |
| 5,846,837 A | | 12/1998 | Thym et al. |
| 5,851,838 A | * | 12/1998 | Vetter et al. ................. 436/170 |
| 5,948,695 A | * | 9/1999 | Douglas et al. .............. 436/518 |
| 6,258,045 B1 | * | 7/2001 | Ray et al. .................... 600/573 |

FOREIGN PATENT DOCUMENTS

| | | |
|---|---|---|
| DE | 1598153 C3 | 11/1973 |
| EP | 0207360 | 6/1985 |
| EP | 0 408 223 A1 | 6/1990 |
| EP | 0 408 223 A * | 1/1991 |
| WO | PCT/US90/01249 | 3/1990 |

OTHER PUBLICATIONS

GDS Ketosite® Blood Ketone (β–Hydroxybutyrate) Test *For In Vitro Diagnostic Use* Catalog No. 301050, Dec. 29, 1993.

* cited by examiner

*Primary Examiner*—Ralph Gitomer
(74) *Attorney, Agent, or Firm*—E. Victor Indiano; Indiano, Vaughan Roberts & Filomena, P.A.

(57) ABSTRACT

A miniaturized, vented capillary channel test strip device for estimating the concentration of an analyte in a fluid is disclosed. The channel transports analysis fluid through interior capillary space defined by the plastic casing of the device. The casing is preferably manufactured by flow injection molding. The capillary channel includes a reaction and a wicking component. Movement of analysis fluid from sampling to reaction to wicking site is enabled by a gradient of capillary force. The gradient is generated by a differential in surface/volume ratio between reaction and wicking component. The reaction component is comprised of a thin reagent film embodying the reactive chemicals, as well as a rehydrating polymer. The polymer absorbs a defined volume of analysis fluid. When the analysis fluid is whole blood, the polymer absorbs blood plasma. Surprisingly and uniquely, cellular component of blood is wholly removed from the reagent film surface by the gradient of capillary force. In this fashion, the reacted test field becomes exposed for visual or instrumented quantification of analyte.

24 Claims, 9 Drawing Sheets

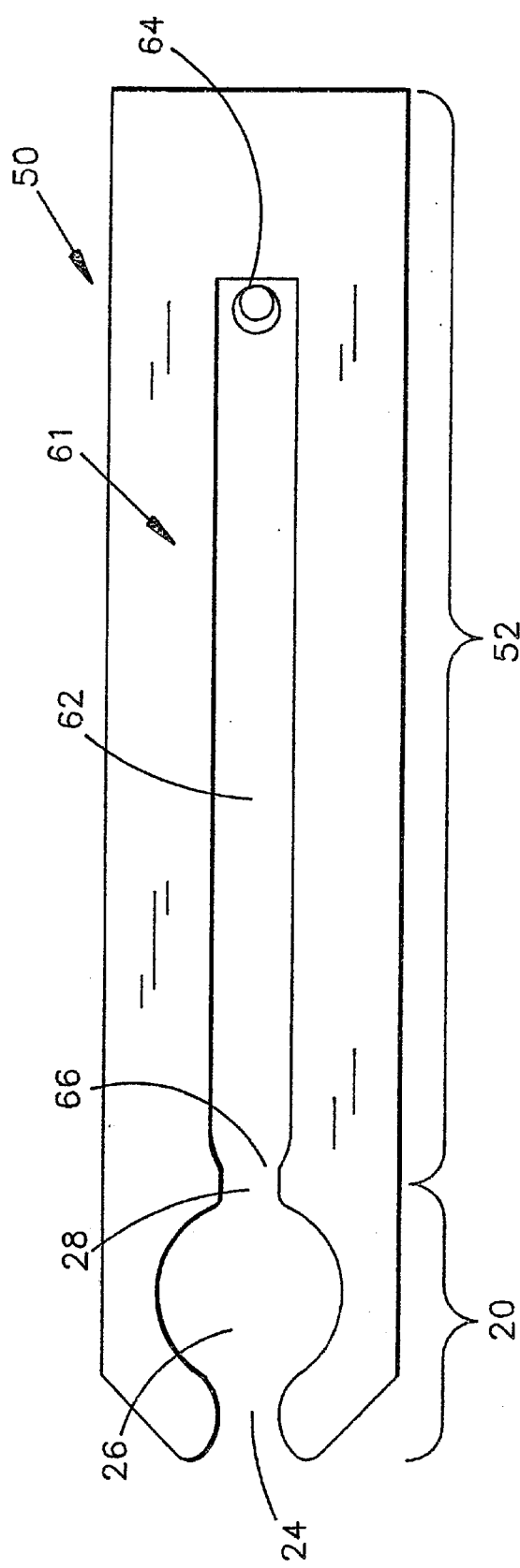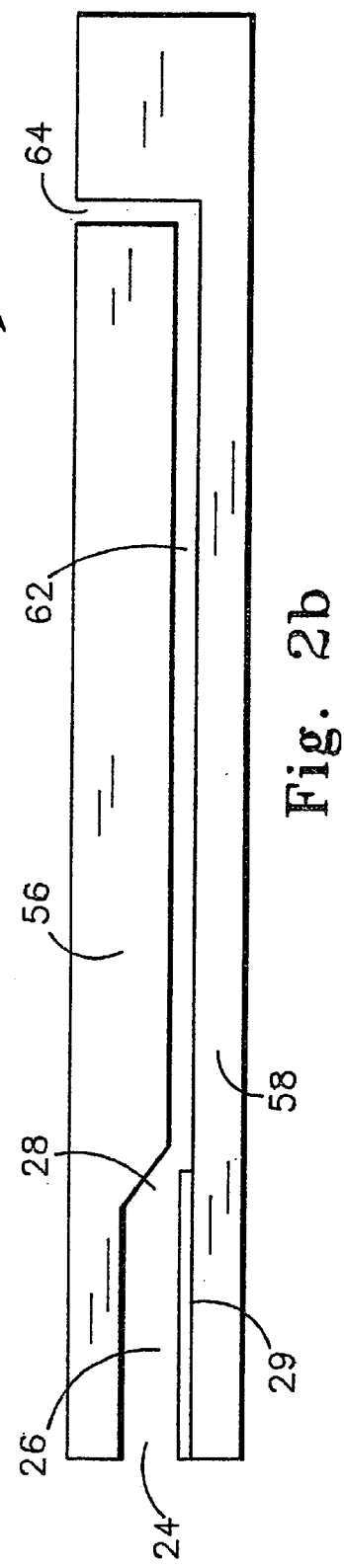
Fig. 2a
Fig. 2b

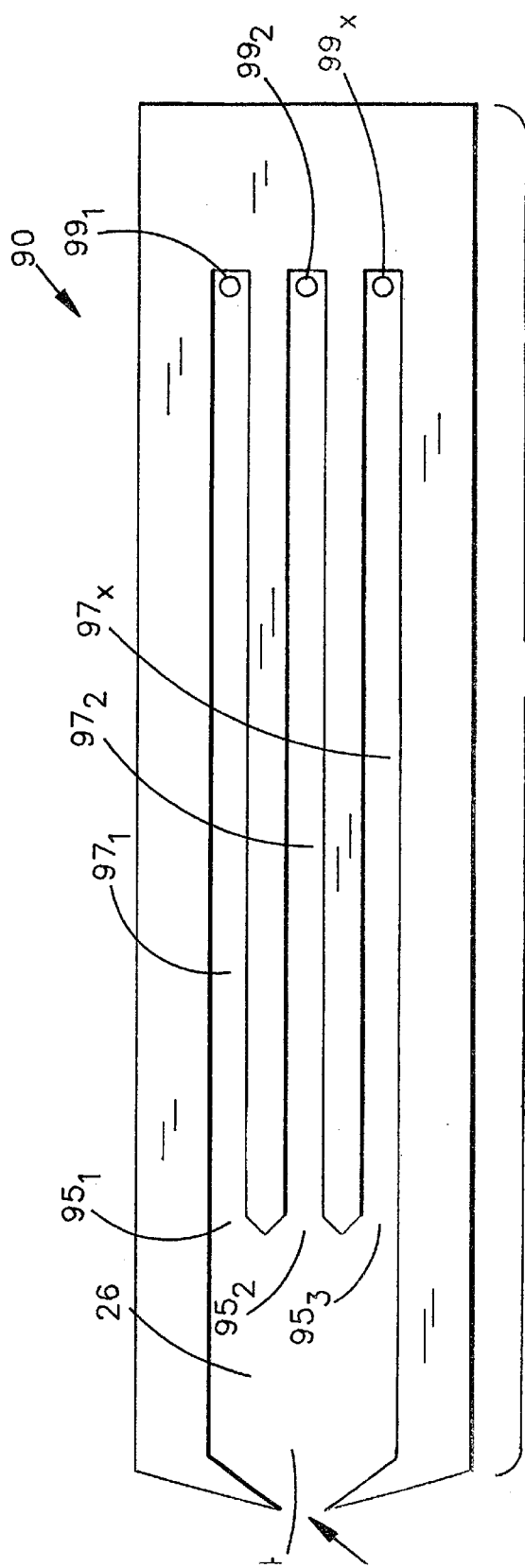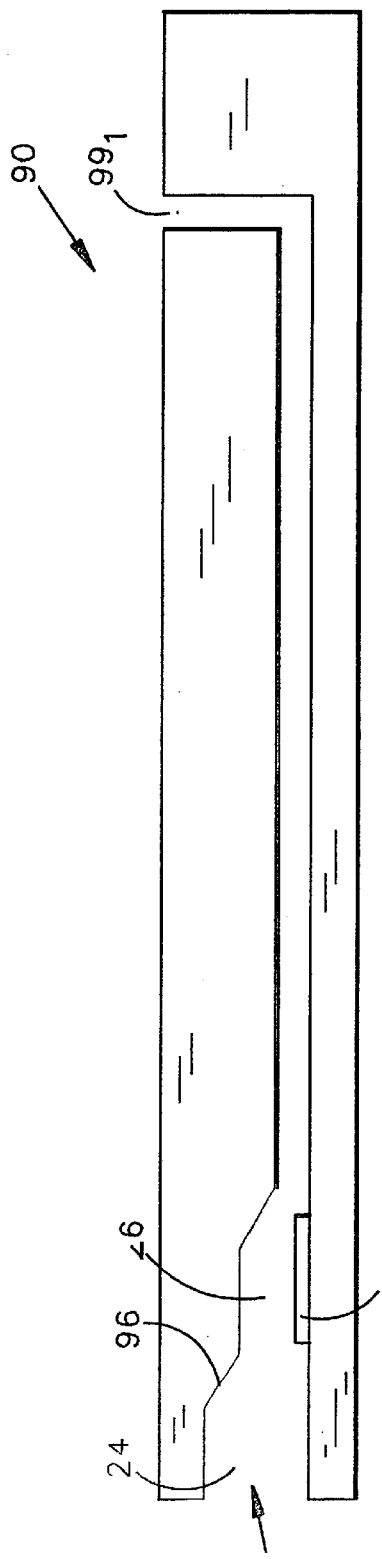
Fig. 6a
Fig. 6b

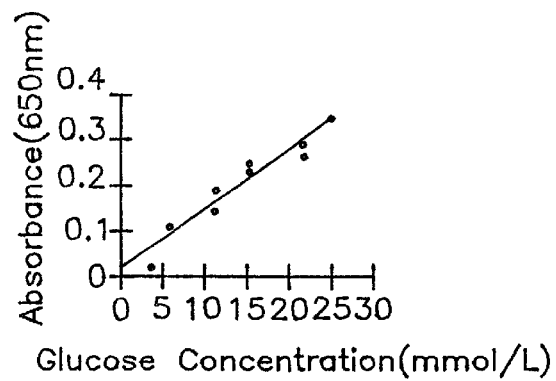
Fig. 10
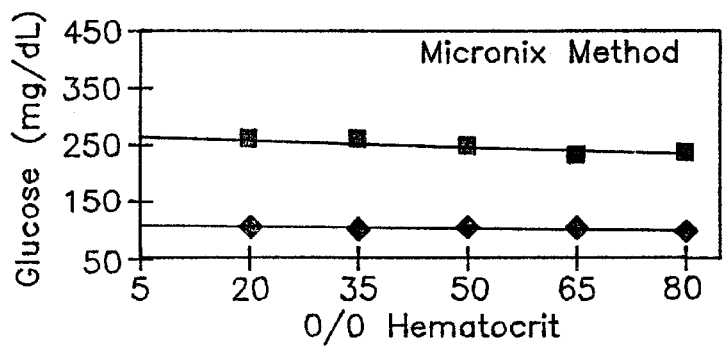
Fig. 11a
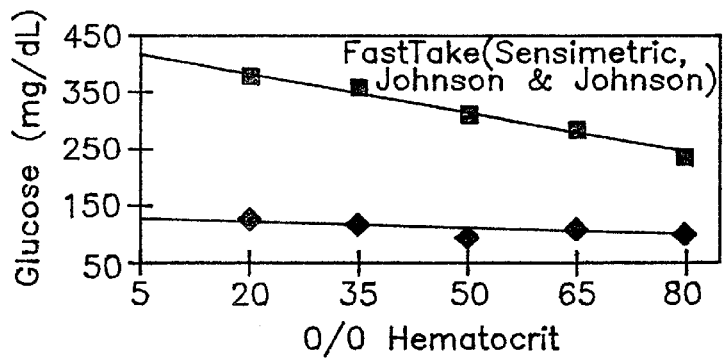
Fig. 11b
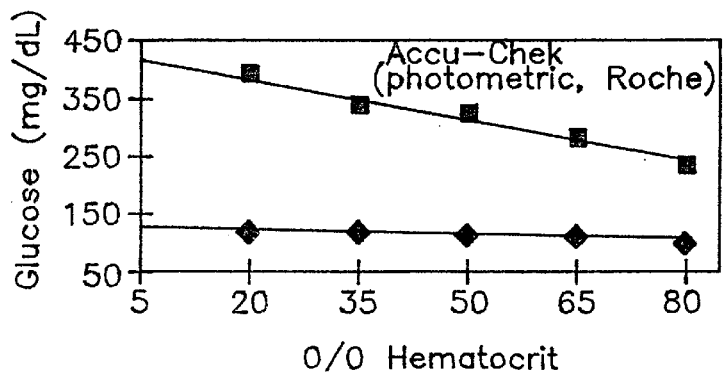

CAPILLARY TEST STRIP TO SEPARATE PARTICULATES

REFERENCE TO RELATED APPLICATIONS

This Application claims the benefit of U.S. Provisional Application No. 60/161,500, filed Oct. 26, 1999.

This invention was made with Government support under one or more of the following grants from the National Institutes of Health. Grant numbers:R43 GM 2145-01 and R43 GM60076.A The Government has certain rights to this invention.

TECHNICAL FIELD OF THE INVENTION

The present invention relates to methods and apparatuses for testing analysis fluids, and more particularly to a microcuvette for analyzing one or more components of a fluid. Significant contemplated applications of the invention are in the biological sciences, especially diagnostic medicine. In this field, analysis fluids would primarily be bodily fluids, notably whole blood.

BACKGROUND OF THE INVENTION

Several dry chemistry technologies have been introduced in recent years for testing of blood specimens at the patient point-of-care (POC). Testing at the POC offers advantages of fast turnaround time, timely intervention, miniaturized and cost effective equipment, and improved patient outcomes. "Dry chemistry" means that the chemical reagents are contained within a test strip device solely in dry, but not in liquid form. Since the reagents are more stable when stored in dry form, products employing dry reagent technology usually have longer shelf life than those using liquid reagents.

In most devices, the reagents are applied to the test strip by some impregnation or coating method whereby a liquid reagent is impregnated or coated onto an integrated reagent-carrying member. The reagent member can be a bibulous material (paper), a membrane, or a reagent film. After evaporation of the reagent solvent, the dry and stable reagent is then contained within a reactive zone, signal member test field of the device. As analysis fluid makes contact with the dry reagents, the reagents are generally at least partially re-solubilized so as to react with the analyte of interest.

The most substantial application of dry technology today is in the field of self-monitoring of blood glucose (SMBG) by millions of diabetics. In this field, both photometric and sensimetric detection technologies are applied for signal quantification. A large portion of metering systems currently used by practitioners employ reflectance photometry. In these meters, light integrating a wavelength absorbed by the colored reaction product of glucose is shined onto the surface of the test field. The test field is preferably mounted on a solid state backing, usually a white plastic material. In this fashion, no light can be transmitted, so that the unabsorbed, scattered portion of the light is reflected.

In contrast to conventional photometry where absorbance of a colored or UV-absorbing reaction product is measured from reduced light transmittance in the direction of the incident light beam, reflectance is typically measured at a location angled away from the direction of incident light. As light of varying incident wavelengths is reflected in different directions, an informed choice must be made as to which ranges of incident and reflective angles to select for obtaining a signal that is most sensitively and most specifically related to concentration. Preferably, the photocurrent detector (photodiode) of the metering device is positioned at a location where unspecific scattering is at a minimum and specific reflectance is at a maximum. However, since specific and unspecific reflectance can usually not be completely spatially separated, pure signals cannot be obtained. For these reasons, measurements made in the reflectance mode do not follow Lambert Beer's law and are therefore fundamentally non-linear. This is in contrast to measurements made in the transmittance mode, which show linear signal-to-concentration responses of absorbance measurements.

Several more recent SMBG devices employ electro-sensimetric detection. The reaction current, measured by a miniature enzyme electrode, is related to glucose concentration and can be monitored amperometrically or by some other means of electrochemical detection. Most reflectance photometric and sensimetric systems employ in the first reaction step the oxygen-dependent enzymic oxidation of glucose by glucose oxidase. This reaction is specific for glucose and produces hydrogen peroxide as a reaction by-product from water and molecular oxygen. Some other systems use glucose dehydrogenase in conjunction with one or more electron acceptors.

In the reflectance photometric systems employing glucose oxidase, the generated hydrogen peroxide is reacted with peroxidase and a chromogen. The oxidized chromophore is then reflectance photometrically quantified by comparison to an on-board standard curve that relates reflectance signal to concentration. Quantification by nonlinear reflectance rather than linear absorbance photometry based on Lambert Beer's law is necessary because the law only holds for clear, non-scattering layers.

Numerous clinical evaluations of currently used glucose metering devices have generally demonstrated adequate analytical performance. However, compromised performance on some of the products, and even outright erroneous results have also been reported. Manufacturers are therefore continually striving to minimize the technical complexity of the systems, maximize operational ease, and improve reliability. Because of the vast global dimension of the SMBG market and the fast growth of diabetes in the world, these efforts have huge socioeconomic implications. At current retail prices of test strips for SMBG, a compliant insulin-dependent diabetic spends in excess of $1000 annually on test strips only, constituting a total global test strip market in excess of $2.4 billion. While this cost can generally be absorbed by citizens or reimbursement systems of the western world, it is prohibitive for most people living in countries other than the western world, where the growth of diabetes is most rampant.

Depending on measurement principle, current test systems have their intrinsic advantages and limitations. An advantage of the reflectance photometric systems is that they measure color. Potentially, this enables both visual and instrumented signal recognition. Visual interpretation can serve as a confidence check for quantitative results provided by the meter. And in markets where meters are not readily available, concentration can still be determined semi-quantitatively. Visual recognition is still well accepted as it was the only method available when SMBG started on a larger scale in the late 1970's. (A significant portion of the world market for glucose test strips is still visual at this time).

Unfortunately, the important feature of visual backup is realized only in a minority of currently marketed systems. This limitation resides in the method by which cellular component of blood is separated from plasma component. In older products, plasma was separated by soak through methods into coated bibulous materials or reagent films. Cells were then manually removed from the site of blood application by either washing or wiping them away, potentially giving rise to significant operator-induced errors. Several newer methods permit separation by means other than washing or wiping. The most frequently used are separation by porous glass fiber fleeces or membranes. In these matrices pore sizes are chosen so that cellular component is held back on the matrix surface, whereas plasma component diffuses through the separating member and into the detection member. Membranes are preferred as plasma separating materials over glass fiber fleeces because they generally absorb less blood. However, one notorious limitation of membranes is that the blood cells can clog pores. More recently, this problem has been largely overcome by using asymmetrical membranes in which pores have larger diameters on the side chosen for blood application as compared to the side dedicated to plasma retrieval.

In most current colorimetric test strips, the separating member is sandwiched against the detection member to provide for ready transfer of plasma into the reagent-impregnated detection member. The reflectance measurement is then made on the side of the test strip opposite to the side of blood application. To keep needed blood volume low, the thickness of the separation member is kept at a minimum. An adverse consequence is that the spatial separation of red cells from the site of measurement is then so small that the cells are incompletely shielded by the thin zone of separation material that is devoid of cells. In instrumented measurements, this "shining through" effect of red cells can, as long as the effect is constant for each measurement, be corrected by calibration or a dual wavelength measurement. However, such corrective methodology makes measurements more complex and less precise. Another corrective method would be to insert an additional, optically dense layer or a contrast material such as titanium dioxide between separation and detection members. But use of this method would further increase blood volume and hence invasiveness. The shining through effect of red cells is particularly disadvantageous for visual interpretation. It is mainly for this reason that most present-day colorimetric test strips cannot be read visually. For the user, the potential of a visual confidence check on digital readouts is thus unfortunately lost.

Another drawback of having a discrete separating member is the well known phenomenon of dependency of test results from the ratio of cellular/plasma component, i.e. the often variable hematocrit. Most current SMBG systems produce results that are inversely correlated with hematocrit. This is because at high hematocrits, red cells can block free diffusion of plasma and hence glucose into the detection member, causing test results to be erroneously low.

Exemplary test strip devices of the present invention all but eliminate hematocrit dependence. (See, FIG. 11). It is hypothesized that absence of significant dependence is the result of supplying the blood to reagent films in a mobile fashion and over a specified period of time, wherein cells are continually removed by capillary force as the blood moves downstream through the collection capillary.

Good progress towards miniaturization was achieved with the advent of the electrochemical sensor methods, not because they would be innately more sensitive (they are not), but because they can function on whole blood as the analysis fluid, thereby obviating the need for a plasma-consuming blood separating member. In some of these products, miniaturization is further aided by provision of capillary fill techniques. Despite these improvements, a major limitation of the sensor methods is that visual backup is completely lost. The user has no other means of accepting a test result than complete reliance on the digitally displayed concentration numbers. This places a very heavy burden on the manufacturer as even minor flaws in test strip architecture or signal conductivity could have disastrous consequences. Also, as is the case with the reflectance photometric methods, signal-to-concentration responses of the sensor methods are not linear, necessitating complex mathematical modeling for device calibration. A further limitation of sensimetric systems is that expansion of the test menu to include analytes other than glucose is quite impractical because a different enzyme electrode would be needed for each additional analyte. By contrast, using the method of the candidate device, test strips for additional analytes could easily be developed by simply substituting detection enzymes in the reagent film. Furthermore, hematocrit dependence in sensor methods can be substantial due to "dilution" of the electrochemical reaction milieu by cellular component. Last not least, the technical sophistication and ensuing manufacturing complexity of the sensor methods makes it much more challenging to manufacture them at low cost.

Measured by its unique performance assets of removal of particulate matter by a capillary force gradient, nano-volume miniaturization, the capacity for transmittance measurement of colorimetric signals, and architectural and manufacturing simplicity, the applicant clear film technology stands on an elevated technological platform for which there is essentially no directly competing prior art to cite.

Previous attempts at technically achieving the desired criteria of testing simplification and miniaturization, so that test results could be easily obtained by practitioners at the POC and even patients in their homes, can conceivably be divided into several enabling technology categories of whole blood separation/plasma retrieval. These are separation by: A) glass fiber matrices (fleeces, "papers") only; B) membranes only; C) combined arrangements of glass fiber (pure or composite) and membrane matrices; D) separations facilitated by agglutinating agents (e.g. lectins, red cell antibodies, carbohydrates, amino acids, etc.); E) separation by soak-in methods into polymers or "gels" (e.g. wiping or washing of cells); F) separation or whole blood delivery augmented by capillary elements.

A method that in some of its principles resembles the applicant technology (and provided significant intellectual fuel for its discovery and development) was disclosed by Azhar et al. (U.S. Pat. No. 5,260,195). However, the core subject of this patent is the description of a manufacturing process from water-insoluble monomers for an acrylic copolymer (latex) that displays the desired properties of reagent film rehydration and filter-less plasma retrieval. Because of the relative water insolubility of the monomers and the copolymer formed from them, this process must rely on the use of organic solvents. Use of organic solvents during manufacturing is undesirable, because of associated environmental, health and cost considerations. The authors of this patent also show a picture of an "apparatus" (a test strip) apparently using the described copolymer. This apparatus is also made subject to one of the claims. A rectangular capillary space is created in the apparatus by lamination of continuous plastic template strips so that the capillary space extends over the entire dimensions of the reagent film. Unfortunately, description of the apparatus and how it might be manufactured is extremely limited. Brief mention is made of the method of blood removal from the capillary vessel.

This is to be performed manually by pressing a cotton swab against one of the two open sides of the capillary and waiting for all sampled blood to be absorbed by the swab. While the method appears to work in principle, it is obviously inflicted with all of the known limitations of manual handling of blood specimens, e.g. dosing imprecision, incomplete reagent and sample mixing, variations in reaction timing, and potential danger of infection.

Accordingly, there is a need for a test strip device that: 1) does not require integration of a blood spreading or plasma separating member within the architecture of the test strip device, i.e. can be performed on less than one (1) microliter of blood; 2) can accommodate all types of photometry as detection principles; 3) streamlines calibration procedures owing to linear signal-to-mass responses of absorbance measurements; 4) is simple by design and thus operationally rugged and analytically precise; 5) features visual backup for users using meters, and visual semi-quantification for users not using meters; 6) can be performed in less than 30 sec by non-technical personnel; 7) can be mass manufactured easily and cost-effectively.

SUMMARY OF THE INVENTION

The exemplary test strip devices disclosed herein are believed to be the first combining colorimetric detection with capillary fill sampling and emptying, and the first measuring transmittance by virtue of using a clear polymer as reagent film, wherein the polymer is dispersed on translucent plastic support. Owing to the partial water permeability of the reagent film, components of aqueous analysis fluid can enter the reagent film upon rehydration of the film by analysis fluid. This process of rehydration of the reagent film enables reaction of a component of the analysis fluid, i.e. the analyte, with the reagent encapsulated in the film.

Pursuant to a first embodiment, there is provided a miniaturized capillary channel test strip device manufactured by plastic flow injection molding. The capillary channel doses and transports analysis fluid, e.g. whole blood within open capillary space extending through the plastic casing of the device. The plastic casing defines the interior capillary dimensions and also serves as a protective housing for a reagent film dispersed within the device The capillary channel includes a collection component and a wicking component, wherein the movement of analysis fluid from sampling site to collection site to wicking site is effected by a gradient of capillary force. The gradient is induced by specialized designs in which the surface/volume ratio of the wicking component is in excess of the surface/volume ratio of the collection component. This differential in surface/volume ratio of wicking component and collection component induces a capillary gradient acting in the downstream direction. Advantageously, the differential in capillary force becomes the main driver for fluid transport through the channel.

The wicking component can either be an absorptive material (e.g. sponge), or it can itself be a capillary or a system of capillaries composed of a plurality of individual wicking capillaries.

The collection component incorporates a planar reagent film (test field). The reagent film contains dried chemical reagents capable of reacting with an analyte, and an inert dried polymer capable of spontaneous rehydration, to thereby absorb a defined portion of an analysis fluid. A unique feature of the invention is that the analysis fluid can be either a homogeneous solution, or a non-homogeneous mixture containing cellular or other particulate matter suspended in the fluid. When the analysis fluid is whole blood, the polymer absorbs a defined volume of blood plasma while inhibiting cellular component of blood from penetrating the reagent film surface. The cellular component is wholly removed from the reagent film by the gradient of capillary force, thereby obviating the need for a separate cell filtering material, and unmasking the reacted test field for visual or instrumented analysis. The instrumented analysis can be performed by fluorimetry, luminescence, reflectance, and preferably by transmittance photometry performed on translucent reagent films.

The above and other objects, features, and advantages of the present invention will become apparent from the following description and the attached drawings.

BRIEF DESCRIPTION OF THE DRAWINGS

FIG. 1b illustrates a central cross-sectional view of the exemplary device depicted in FIG. 1a;

FIG. 2a illustrates a top view of an exemplary device employing an open capillary with varying height dimension to generate a gradient of capillary force;

FIG. 2b illustrates a central cross-sectional view of the exemplary device depicted in FIG. 2a;

FIG. 6a illustrates a top view of a longitudinal cross section of an exemplary device featuring two discrete transition steps for facilitating surface expansion and capillary force differential;

FIG. 6b illustrates a side view of a longitudinal cross section of the exemplary device depicted in FIG. 6a;

FIG. 10 depicts linear signal-to-concentration photometric response of a manually fabricated candidate device measuring transmitted light;

FIGS. 11a, 11b and 11c summarize an experiment to evaluate hematocrit dependence for the candidate and two major commercial glucose monitoring devices.

DETAILED DESCRIPTION OF EXEMPLARY EMBODIMENTS

Figure 1A:
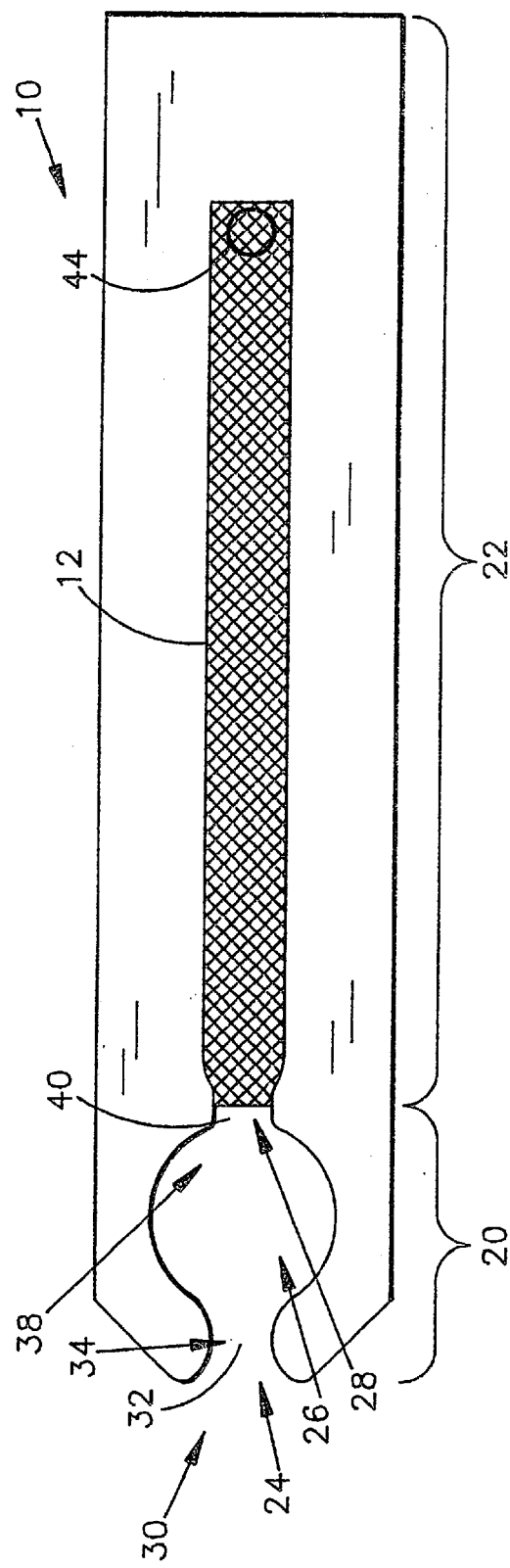
FIG. 1a illustrates a top view of an exemplary device using an absorbent material for removal of cellular or particulate matter and excess analysis fluid.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Figure 1B:
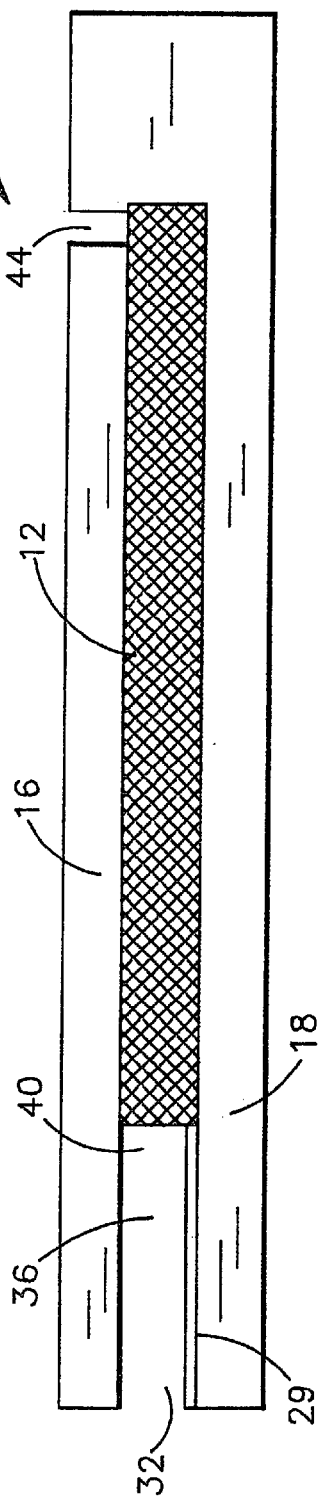

An exemplary test strip device 10 utilizing an absorbent material 12 is depicted FIG. 1. In general, the exemplary test strip device 10 includes a first plate 16 coupled to a second plate 18 that in combination define a collection component 20 and a wicking component 22. The collection component 20 of the exemplary test strip device 10 includes an entry capillary 24, a collection capillary 26, and an exit capillary 28.

The entry capillary 24 is generally defined by an entry vessel 32 having an inlet 30. The entry vessel 32 and inlet 30 are generally structured to exert capillary forces upon fluid applied to the inlet 30 and draw fluid into the entry vessel 32. Similarly, the collection capillary 26 is generally defined by a collection vessel 36 having an inlet 34 that is coupled to the entry vessel 32. The collection vessel 36 and inlet 34 are generally structured to exert capillary forces upon fluid in the entry vessel 32 and to draw the fluid from the entry capillary 24 into the collection vessel 36. Further, the exit capillary 28 is generally defined by an exit vessel 40 having an inlet 38 that is coupled to the collection vessel 36. The exit vessel 40 and inlet 38 are generally structured to exert capillary forces upon fluid in the collection vessel 36 and draw the fluid from the collection capillary 26. As a result of the above structure and interconnection of the entry capillary 24, the collection capillary 26, and the exit capillary 28, fluids sampled via the inlet 30 of the entry capillary 24 flow into the entry capillary 24, to the collection capillary 26, and to the exit capillary 28.

The collection capillary 26 of the test strip device 10 also includes a reagent film 29 that coats at least one inside wall of the collection vessel 36. The reagent film 29 of the exemplary test strip device 10 has a wet thickness between 50 and 400 microns and generally includes specific reagents to react with the analyte of interest. However, the reagent film 29 may also be implemented without reagents such that reagent film 29 is merely hydrated with sampled fluid to permit collection, transport and future analysis of the sampled fluid.

The wicking component 22 is positioned downstream from the exit capillary 28 and includes an absorbent material 12 that is in communicative fluid contact with the exit capillary 28. In particular, the absorbent material 12 of the exemplary test strip device 10 is positioned adjacent to the reagent film 29. The absorbent material 12 generally draws fluid over the reagent film 29 of the collection component 20 through the exit capillary 28. As fluid is drawn through the collection component 20, a discrete portion of the fluid having the analyte of interest diffuses into the reagent film 29. Therefore, in the exemplary test strip device 10 having reagent in the reagent film 29, the diffusion of fluid into the reagent film 29 initiates a chemical reaction between the analyte of interest and the reagent of the reagent film 29. Conversely, for an embodiment of the exemplary test strip device 10 without reagents in the reagent film 29, the reagent film 29 merely collects and retains the analyte which may be analyzed at a later time.

The wicking component 22 also includes a venting channel 44 that essentially provides a pressure outlet. In general, the venting channel 44 enables gases to escape or vent from the wicking component 22 as the wicking component 22 fills with fluid. Without the venting channel 44, pressure within the wicking component 22 increases as the wicking component 22 fills with fluid, thus counteracting the capillary force and absorbent forces created by the absorbent material 12.

For reactions having sufficient sensitivity to produce a desired photoelectric signal, only one inside wall of the collection capillary 26 is coated with reagent film 29. In the case of less sensitive reactions, signal-to-mass response can be increased by coating additional walls of the collection capillary 26 with reagent film 29. Similarly, if reagent film 29 contains no reagent, then additional walls of the collection capillary 26 may also be coated with the reagent film 29 in order to collect additional analyte for future analysis.

In a preferred collection/testing procedure, sampling of the fluid is discontinued when the collection component 20 is filled with the fluid being sampled. At this time the fluid has preferentially reached the absorbent material 12 of the wicking component 22. The wicking component 22 then draws the sampled fluid through the collection component 20 and across the reagent film 29. In the exemplary embodiment, the absorbent material 12 essentially empties the collection component 20 by absorbing the fluid by virtue of absorptive and capillary forces of the absorbent material 12.

The speed by which the fluid is drawn out of the collection component 20 by the absorbent material 12 is primarily a function of the average pore size and pore density of the absorbent material 12. With the most effective wicking materials currently available, such as high density cellulose, polyethylene or polypropylene sponges, the entire process of sampling and wicking can be accomplished in as little as five to six seconds.

Referring now to FIGS. 2a and 2b, there is depicted another exemplary test strip device 50. Test strip device 50 of FIGS. 2a and 2b is quite similar to the test strip device 10 of FIGS. 1a and 1b. Accordingly, like components of the two devices are referenced with the same numerals and only the differences are discussed in detail below. In particular, the test strip device 50 includes a first plate 56 coupled to an second plate 58 that in combination define a collection component 20 and a wicking component 52.

Similar to the wicking component 22 (FIG. 1), the wicking component 52 (FIG. 2) is coupled to the exit capillary 28 of the collection component 20. However, unlike the wicking component 22, the wicking component 52 of FIGS. 2a and 2b does not include absorbent material. Instead the wicking component 52 is implemented with at least one wicking capillary 61 having a wicking vessel 62 with a venting channel 64 and a wicking inlet 66 coupled to the exit capillary 28. The wicking vessel 62 and wicking inlet 66 are structured to exert capillary forces upon fluid in the exit capillary 28 and draw the fluid from the exit capillary 28 into the wicking vessel 62 and thereby draw the fluid from the collection component 20.

In addition, the venting channel 64 of the wicking component 52 essentially provides a pressure outlet that enables gases to escape or vent from an end of the wicking vessel 62 that is distal from the wicking inlet 66 as the wicking vessel 62 fills with fluid. Without the venting channel 64, pressure within the wicking vessel 62 increases as the wicking vessel 62 fills with fluid, thus counteracting the capillary force created by the wicking component 52.

Preferably, the total capillary force generated by the at least one wicking capillary 61 significantly exceeds the total capillary force generated by entry capillary 24, collection capillary 26, and exit capillary 28. In general, this larger capillary force is achieved by structuring the wicking capillary 61 such that the wicking capillary has a greater ratio of surface area per unit length to volume per unit length than the collection component 20. In the exemplary test strip device 50, this is achieved by structuring the wicking capillary 61 with a smaller height dimension than the collection component 20. Since total capillary force is positively correlated with total activated capillary surface, capillary force acting in the downstream direction will be larger than in the upstream direction. The ensuing pumping action in the downstream direction of the exemplary test strip device 50 therefore pulls all sampled fluid into the interior space of the wicking capillary 61. Consequently, partial back flow of fluid in the upstream direction, as potentially effected by counter capillary force exerted by the emptying collection component 20, is prevented.

Figure 5:
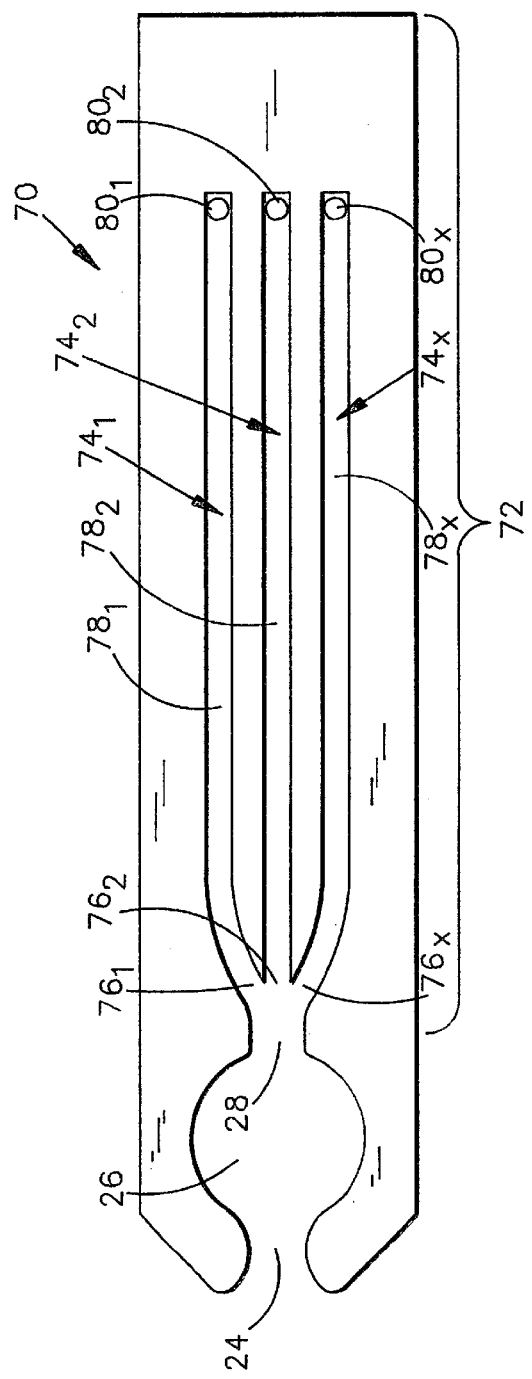
FIG. 5 shows a top view of an embodiment using a plurality of wicking capillaries.

Another way of increasing the capillary force of the wicking component is shown in FIG. 5. In particular, the test strip device 70 of FIG. 5 is quite similar to the test strip device 50 of FIG. 2 except the wicking component 72 is implemented with a plurality of wicking capillaries $74_1, 74_2, \ldots 74_X$. Each of the wicking capillaries $74_1, 74_2, \ldots 74_X$ includes a separate wicking inlet $76_1, 76_2, \ldots 76_X$ coupled to the exit capillary 28, a separate wicking vessel $78_1, 78_2, \ldots 78_X$, and a separate venting channel $80_1, 80_2, \ldots 80_X$. In general, the plurality of wicking capillaries $74_1, 74_2, \ldots 74_X$ may be structured to better increase the surface/volume ratio than the wicking capillary 61 of FIGS. 2a and 2b.

The test strip device 90 of FIGS. 6a and 6b further illustrates that the capillary forces of the collection component 92 may also be adjusted to ensure an increasing capillary gradient from inlet 94 through the collection component 92. In general, the test strip device 90 of FIGS. 6a and 6b is quite similar to the test strip device 70 of FIG. 5. One difference between the two test strip devices is the test strip device 90 does not include an exit capillary between the collection capillary 94 and the wicking capillaries $97_1, 97_2, \ldots 97_X$ of the wicking component 96. In particular, each of the wicking capillaries $97_1, 97_2, \ldots 97_X$ includes a wicking inlet $95_1, 95_2, \ldots 95_X$ coupled to the collection component 92 and a venting channel $99_1, 99_2, \ldots 99_X$ distal from the wicking inlet $95_1, 95_2, \ldots 95_X$. Another difference between the two test strip devices is that the height of the collection component 92 is decreased by two transition steps 96, 98 in the downstream direction. By decreasing the height of the collection component 92 in such a manner, the collection component 92 exerts greater capillary force upon the fluid as the fluid is drawn through the collection component 92 to the wicking component 96.

Figure 7:
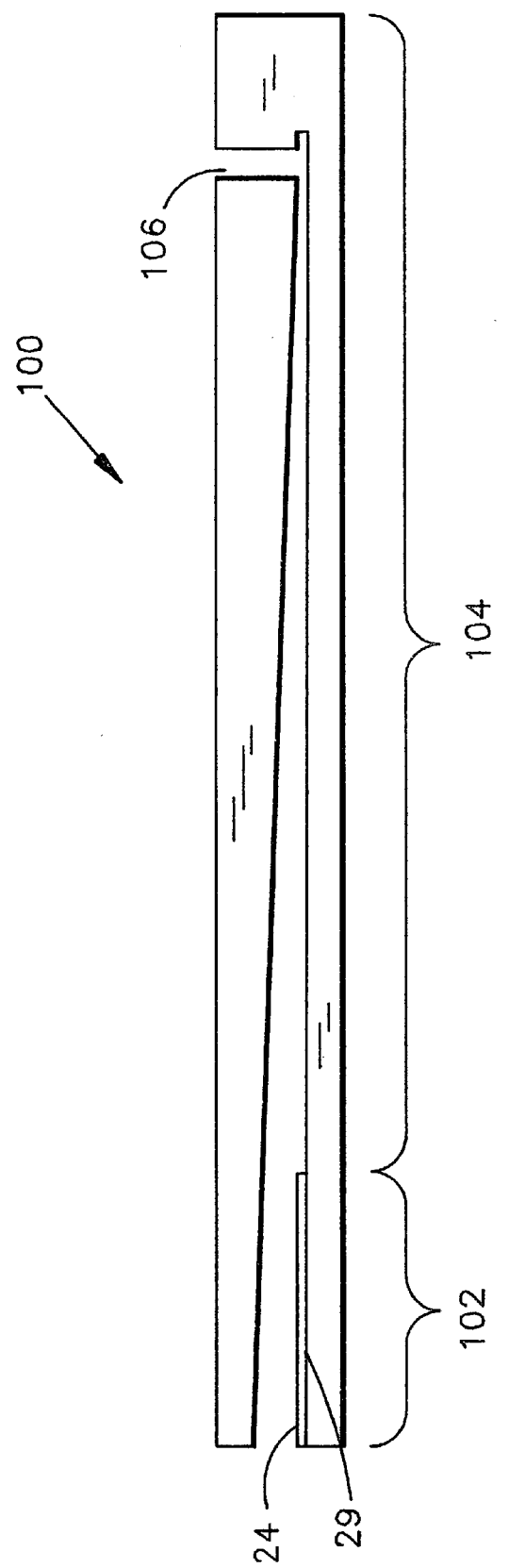
FIG. 7 shows a longitudinal cross-sectional view of a device similar to the device depicted in FIG. 6a and FIG. 6b that features continuous restriction of the capillary height dimension.

Yet another test strip device 100 is illustrated in FIG. 7. In general, the test strip device 100 of FIG. 7 is quite similar to the test strip device 90 of FIG. 6. However, instead of decreasing the height in steps over only the collection component, the height of both the collection component 102 and the wicking component 104 are continuously decreased in the downstream direction. By decreasing the height of both the collection component 102 and the wicking component 104 in such a continuous manner, an increasing capillary force is generally exerted on the fluid as the fluid flows through the collection component 102, into the wicking component 104, and toward the venting channel 106. This generally increasing capillary force helps to prevent fluid backflow through the test strip device 100.

Both the exemplary test strip devices with and without absorbent material produce desirable results. However, the test strip devices without absorbent material are preferred over the test strip devices with absorbent material, because potential adverse influences on test results caused by inconsistencies of the absorbent material 12 are obviated. Another advantage of using a capillary as the wicking component rather than an absorbent material is that the only material needed in addition to the flow injection molded plates is the reagent film 29. This feature enables a hitherto unparalleled level of simplicity and potential for miniaturization.

Figure 4:
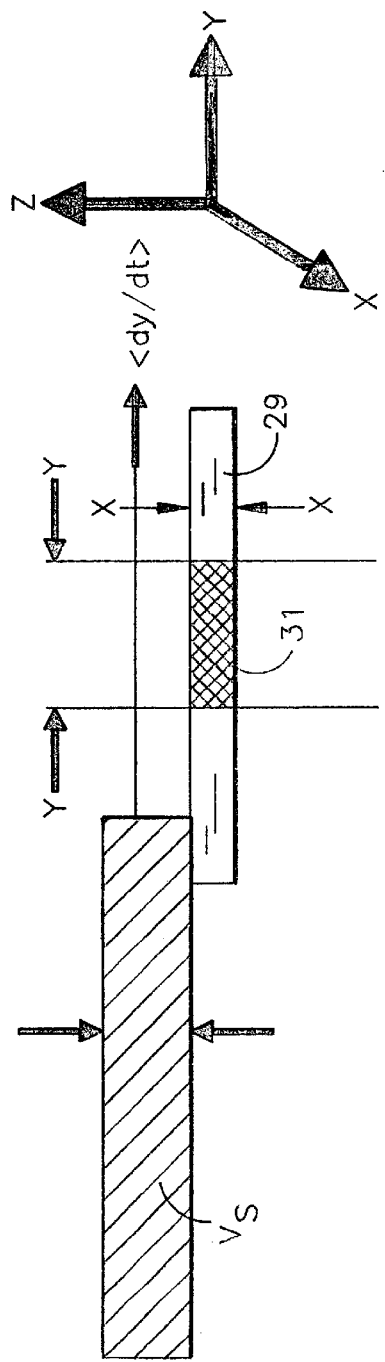
FIG. 4 depicts a schematic presentation of a longitudinal cross section through sample layer and reagent film to illustrate downstream flow of analysis fluid and mass transport of analyte into reagent film.

In the above embodiments, the speed of fluid flow through the collection component can be modulated by varying diameter and length of the entry capillary and the exit capillary of the collection component. Incoming fluid flow through the collection component 20 of the exemplary test strip device 10 is somewhat enhanced when the test strip device 10 or 50 is held in a vertical position. However, the method also functions when any of exemplary test strip devices is held horizontally or with the entry capillary 24 pointed downward. The net result of the above modes of operation is that the reagent film 29 only shown in FIG. 4 is completely cleared of particles (e.g. red cells when sampling blood). As the excess fluid and any particles therein are removed from the collection component, the reagent film 29 and test field 31 becomes fully exposed and the reaction color can be monitored either instrumentally, visually or both.

Surprising, and fundamentally unique to the subject invention is the discovery that this type of capillary force-enabled wicking action, in combination with chemically appropriate reagent film 29 and correctly selected wicking components, completely sweeps the collection component and reagent film 29 free of red cells when sampling blood. This can be concluded from the finding that all red color has disappeared from the reagent film 29 once all excess blood has been absorbed into the wicking component.

Reagent Film

Polymeric materials achieving the separation of plasma from whole blood have been described in the scientific and patent literature. Four types of materials have been used. Cellulose ester and nylon membranes; polytetrafluoroethylene (PTFE, Teflon) stretched membranes; latex and other coatings; glass fiber fleeces or "papers". Drawbacks of membranes are clogging of pores with associated slow or insufficient plasma delivery. The need to manually wash or wipe away red cells has been a problem with coatings. Advantages of glass fiber papers are low price, availability from several manufacturers, and proven performance. Disadvantages in comparison to coatings and membranes are slower speed of separation and larger sample requirements. The fundamental limitation of presently marketed colorimetric test strips based on these separation principles is that all of them require, in addition to a signal member, some sort of a porous cell/plasma separating member which by itself absorbs plasma, thereby adding to the amount of blood needed and impeding present-day attempts at reducing invasiveness via method miniaturization.

A versatile glass fiber separation technology needing only a few microliters of blood has been pioneered and patented by Micronix (U.S. Pat. No. 4,883,764 entitled "Blood Test strip"). A surprising recent discovery made in our laboratory was that red cells can be wholly removed from certain hardened polymer surfaces (films) when the sampled blood is pulled over these surfaces by capillary force. Advantageously, the process is accompanied by absorption of a defined volume of blood plasma into the polymer of the reagent films 29. Since certain exemplary films 29 also contain detection reagents, reaction colors can be monitored without interference by red cells.

Advantageously, several polymeric film-forming materials displaying the desired properties of plasma permeability and light transparency are commercially available. They can be both natural (protein- or polysaccharide-based), or synthetic polymers, water-soluble or water-insoluble (Table 1). Water insoluble polymers can be used as film formers either after dissolving the polymer in an organic solvent, or by using a two-phase dispersion of the polymer. A large range of stabilized aqueous dispersions ("latex") is commercially available. In these products, the insoluble polymers are finely dispersed as micro-spheres (latex particles). The products are abundantly used in the adhesive, coating and other industries. Concentrations (weight/weight) of the polymers in film-forming liquid mixtures are generally in the range of 10% to 55%. The viscosity range for best coating properties is between 1000 and 3000 mPa.s.

Rehydration for the water-soluble and -insoluble polymer films is fundamentally different. In the case of water-soluble polymers analysis fluid penetrates the reagent film by partially dissolving the film surface. In the case of water-insoluble polymers, rehydration occurs due to diffusion of analysis fluid into inter-particle spaces ("interstices"). In either case, uniformity of reaction color over the entire viewed test field area, generated from analyte reaction with a dye substrate, is generally better than with bibulous materials or membranes, because of the much larger and hence less homogeneous fiber micro-structures of these materials. These structures can cause inhomogeneities of reaction color due to micro-capillary and micro-chromatographic effects giving rise to disproportionate distribution of reagents and/or reaction color.

TABLE 1

CANDIDATE FILM FORMING POLYMERS

| FILM CHARACTERISTICS | FILM-FORMING POLYMERS |
|---|---|
| Water-soluble, natural | gelatin; dextran; starch; starch ethers; and cellulose ethers. |
| Water-soluble, synthetic | poly(vinyl alcohol), PVA esters; poly(N-vinyl pyrrolidone); poly(vinyl sulfonate); polyalkylene esters, ethers and oxides; some acrylate, methacrylate esters, acrylamides, some styrene, maleate and vinyl pyridine polymers. |
| Water-insoluble/ organic solvent | cellulose esters (acetates, nitrates); polyesters. |
| Water-insoluble/ dispersions | vinylesters, e.g. Vinylacetate, vinylpropionate; polymers of acrylic acid, acrylamide, methacrylic acid; alkene and alkadiene polymers, e.g. ethylene, propylene, isobutylene, butadiene-based polymers; polymers of styrene and derivatives; urethane hybrid polymers. |

Advantages of Capillary Sampling

Capillary sampling of fluid via the collection component and wicking component contributes three major advantages to the candidate test strip devices. In particular, the capillary sampling results in controlled specimen dosing, filter-less plasma separation, and extensive potential for miniaturization. In most conventional test strips, the analyst provides analysis fluid to the test field manually by contacting the strip with a drop or unspecified portion of a drop of blood. This technique has significant limitations with respect to constancy of volume applied and locations on the test field surface contacted by the drop. Consequences can be under-sampling or over-sampling, or heterogeneous distribution of analysis fluid and hence reaction color. As a result, some of these methods can be fraught with substantial test-to-test and operator-to-operator variances. The problem can be ameliorated by applying test sample with a manual or semi-automated pipetting device. However, using a pipetting technique would make a method technically more complex and demanding, and may still not overcome all challenges of uniform sample application and distribution.

By contrast, the capillary sampling of the collection component 20 enables high constancy of specimen dosing and distribution, because contact of analysis fluid with test fields is uniform as it is geometrically and kinetically definable by the very design specifications of the collection component 20 and the wicking components 22, 52. In generally, any clear plastic material can be used for the plates 16, 18 that define the capillaries of the collection component 20. Preferred materials for the plates 16, 18 include polycarbonate (PC), polymethylmethacrylate (PMMA, PLEXIGLASS"), or polystyrene. The collection component serves both as a transport means for the analysis fluid, as well as a protective housing for the reagent film 29. A fluid spreading layer is not required as the layer of fluid in communicative fluid contact with the reagent film 29 is specified by the interior dimensions of the collection component 20. The reagent film 29 itself essentially functions as a miniaturized solid-state cuvette.

A major advantage of the exemplary test strip devices over prior test strip devices when used for analysis of blood components resides in their capacity to retrieve plasma from whole blood via filter-less diffusion of plasma into polymer-based films 29, combined with removal from the films 29 of cellular component by a gradient of force. In this mode of operation, only a single polymeric reagent film 29 with a thickness in the micrometer range is required for the simultaneous accommodation of both plasma acquisition and chemical analysis.

Theory of Operation

Figure 3:
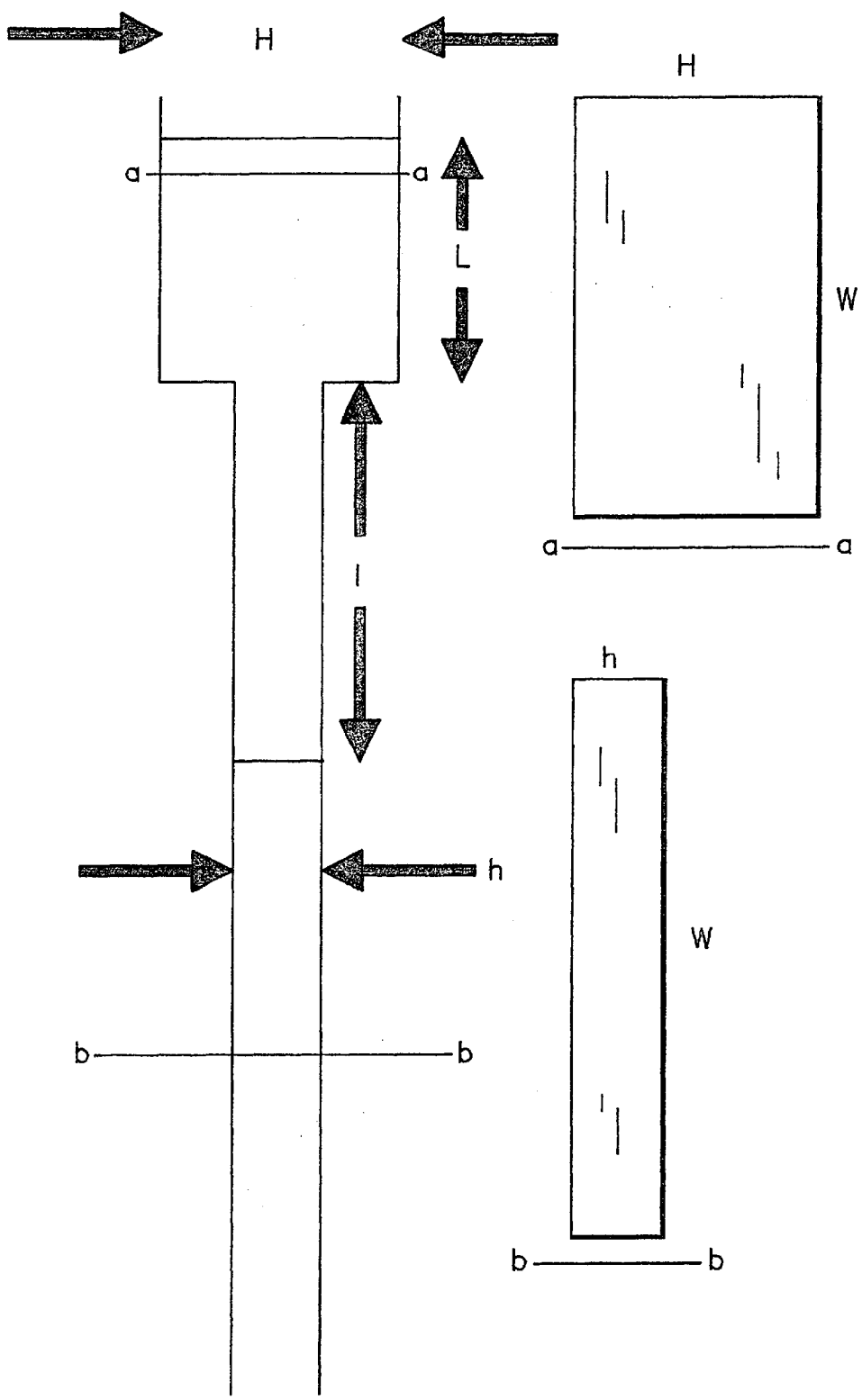
FIG. 3 depicts a schematic illustrating fluid surface expansion effected by transition of analysis fluid from collection capillary to a wicking capillary having at least one restricted interior dimension.

A theoretical explanation for the functionality of the wicking capillary system is provided by relating surface expansion and surface tension to ensuing gains in surface free energy (FIG. 3) and by comparing relevant capillary and gravitational forces. This functionality is graphically represented in FIG. 3.

For purposes of computational simplicity, it is assumed that "reaction capillary" R and "wicking capillary" K both have rectangular cross sections and equal channel width (W), differing only in their height and length dimensions. Under these assumptions, a decrease in volume in R of $\Delta V = W \cdot H \cdot \Delta L$ occurs when the level of analysis fluid in R sinks by the increment $\Delta L$. This decrease is identical to the volume increase in K of $\Delta V = W \cdot h \cdot \Delta 1$. From $W \cdot H \cdot \Delta L = W \cdot \Delta L = W \cdot h \cdot \Delta 1$ follows $\Delta 1 / \Delta L = H/h$, or $\Delta 1 = \Delta L \cdot H/h$.

The lowering of the fluid level in R creates new capillary active surface in R of $\Delta A_R = \Delta L \cdot 2(W+H)$. Simultaneously, capillary active surface in K is reduced by $\Delta A_K = \Delta 1 \cdot 2(W+h)$. It follows that $\Delta A = \Delta A_K - \Delta A_R = \Delta 1 \cdot 2(W=h) - \Delta L \cdot 2(W+H) = 2\Delta L \cdot W(H/h-1)$. A gain in surface free energy can then be computed amounting to $\Delta E = \Delta A \sigma_{H2O}$, where $\sigma_{H2O}$ [$72 \cdot 10^{-3} N \cdot m^{-1}$] is the surface tension of water as applicable to aqueous analysis fluids.

The capillary force $F_C$ [N] then results from $F_C = \Delta E/\Delta L = 2W(H/h-1) \cdot \sigma_{H2O}$.

The corresponding gravitational force $F_G$ can be defined as $F_G = (W \cdot H \cdot L + W \cdot h \cdot 1) \cdot \rho \cdot g$, where $\rho$ is the specific gravity of water and g is the acceleration due to gravity. For the condition at the start of flow into K, the expression reduced to $F_G = W \cdot H \cdot L_0 \cdot \rho \cdot g$, where $L_0$ is the level of fluid in R at the start of flow into K.

Comparative computation of $F_C$ and $F_G$ by numerically substituting chosen dimensions of capillary cavities for manually fabricated test strip prototypes permits an estimate of the relative magnitude of capillary vs. gravitational force:

$$W=10^{-2}[m] H=2*10^{-4}[m] L_0=5*10^{-3}[m]$$

$$\rho=10^3[kg*m^{-3}]$$

$$g=9.81[m/sec] h=4*10^{-5}[m] \sigma_{H2O}=72*10^{-3}[N/m^{-1}]$$

Substitution of the given parameters into the above derived formulas for $F_C$ and $F_G$ yields: $F_G=9.81 \cdot 10^{-5}$ N, and $F_C=580 \cdot 10^{-5}$ N. The computation demonstrates that even in the current non-optimized test strips, capillary exceeds gravitational force by a factor close to sixty (60). This is in compliance with our experimental findings that the speed of capillary fill with whole blood as the analysis fluid is independent of the angle at which the test strip is held to a micro-droplet of blood.

In the embodiment using a wicker material, the speed by which the blood is drawn out of the capillary space is primarily a function of the average pore size and pore density of the wicker material. With the most effective wicker materials currently available, such as high density cellulose, polyethylene or polypropylene sponges, the entire process of sampling and wicking can be accomplished in as little as 5–6 seconds. The speed of blood flow through the capillary space can be further modulated by varying diameter and length of entry and exit capillaries.

Unexpected and fundamentally unique to the technology is our discovery that this type of capillary force-enabled wicking action, in combination with chemically appropriate reagent films and correctly selected capillary elements, completely sweeps the reaction capillary free of cellular component. This can be concluded from consistent findings that all red color has disappeared from reagent films once all excess sampled blood is absorbed inside the wicking component.

Remarkably, this delicately balanced process of filter-less plasma isolation via diffusion of plasma into polymeric film, accompanied by removal of cellular component from the film surface by forced capillary flow has hitherto not been unveiled. It is believed that this technology has a substantial number of potential applications in the medical, veterinary and other biological sciences.

The functionality of the measurement process can be plausibly mathematically defined if the following fundamental conditions are met:

1) defined and reproducible architecture of capillary channel system

Referring now to FIG. 4, under these conditions a residence time for the analytical sample, over that zone (test field 31) of the "film", can be defined that is upon measurement illuminated by the cross-section of the photometric light beam (FIG. 4). The designated planar dimensions of the cross-section of the light beam are y [mm] in the direction of flow, and x [mm] perpendicular to the direction of flow. The capillary channel segment above the illuminated portion of the 'film' has the designated dimensions x', y', and z' in the directions of the chosen coordinate system. The residence time ($\tau$) of the portion of analytical sample over the later illuminated, measured volume fraction of 'film' then is:

$$\tau = V_s/v,$$

where $V_s$=sample volume [mm$^3$], and v=rate of flow [mm$^3 \cdot$sec$^{-1}$]=$z' \cdot x' \cdot$<dy/dt>, where $z' \cdot x'$=cross section of capillary channel segment [mm$^2$] above the measured cross section of 'film' (y·x) [mm$^2$], and <dy/dt>=average speed of flow [mm·sec] across this channel segment (parabolic velocity profile). During the so defined residence time of analysis fluid above the measured volume of 'film', mass transfer into 'film' occurs of an analyte component (i). The flux of the analyte component i, $j_i$, perpendicular to the phase boundary ('film' surface) is given by:

$$j_i = \beta(c_{i,b} - c_{i,g}),$$

where $j_i$ flux [mole·sec$^{-1} \cdot$mm$^{-2}$], $\beta$=mass transfer coefficient [mm·sec$^{-1}$], $c_{i,b}$=concentration of analyte i in the analysis fluid [mole·mm$^{-3}$], and $c_{i,g}$=concentration of analyte i at upper boundary of 'film' [mole·mm$^{-3}$]. The total amount $a_i$ of analyte component i transferred during residence time $\tau$ from analysis fluid into 'film' over the cross section y·x [mm$^2$] is given by the equation:

$$a_i = j_i \cdot y \cdot \tau = \beta \cdot y \cdot x \cdot \tau (c_{i,b} - c_{i,g}).$$

If $\beta$, y, x and $\tau$ are kept constant and $c_{i,g}$ is much smaller than $c_{i,b}$, where k is a constant (k=$\beta \cdot y \cdot x \cdot \tau$). This relationship is valid under the above conditions 1) through 5), both in the case of diffusion controlled mass transfer (homogeneous water swellable polymer films), as well as in the case of bulk flow through inter-particle interstices effected by capillary forces, superimposed by diffusion into rehydrating particles (layer of particles formed by drying of a dispersion).

If the total amount of transferred analyte component i ($a_i$) reacts quantitatively with excess reagent in the 'film', then the absorbance A (measured on transparent reagent films) at a wavelength characteristic for the reaction product of i with the reagent is linearly related to concentration (Lambert Beer's law):

$$A = \ln I_0/I = \epsilon \cdot a_i (x \cdot y)^{-1},$$

where $I/I_0$=transmittance, $\epsilon$=molar extinction coefficient [mm$^2 \cdot$mole$^{-1}$]

These derivations illustrate that measurements taken in the absorbance mode solely depend on the amount of analyte i transferred across the area x·y, and do not depend on the distribution of i over the thickness dimension (z) of the reagent film due to subsequent diffusion in the z-direction. This is in contrast to reflectance measurements taken on reacted test field surfaces, which are fundamentally diffusion dependent. Thus, the independence of reaction signals from analyte and reaction product distribution in the z-direction makes measurement in the absorbance mode intrinsically more precise than measurement in the reflectance mode.

Figure 9A:
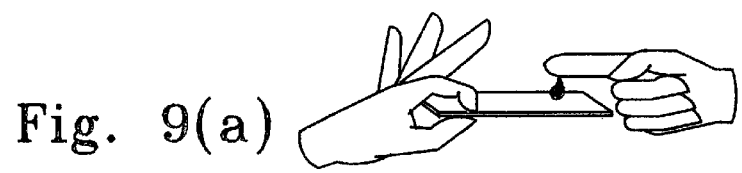
FIGS. 9a, 9b and 9c illustrate the use of the device in routine analysis of a miniature finger stick blood specimen.
Figure 9B:
Figure 9C:
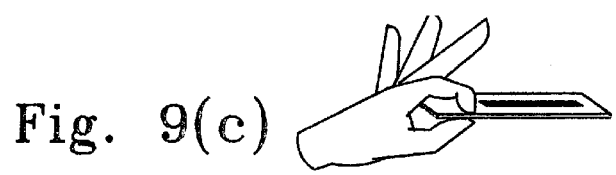

Turning now to FIGS. 9a–9c, the capillary doses procedure is illustrated. FIG. 9a illustrates that the first step in the procedure is to apply blood that emerges from the patient as a result of a fingerstick to the entry capillary. When blood from the fingerstick has filled the reaction capillary, the patient's finger is removed from engagement with the device, as shown in FIG. 9b. Finally, as shown in FIG. 9c, the test strip is inserted into the meter as soon as the reaction capillary has emptied.

FIG. 10 is a graph that illustrates absorbance of light at 650 nm as a function of glucose concentration, thereby illustrating the dose response of experimental capillary test strips for blood glucose. Glucose concentrations in whole blood were 3, 6, 5.5, 11.7, 16.4, 22, and 25.6 mmol/L. The reagent concentrations in 83% UCAR-462 dispersion were: glucose oxidase 200 U/mL; peroxidase 100 U/mL; tetramethylbenzidine (TMB) 20 mmol/L; octyl sulfate 22 mmol/L; sodium alginate 0.5 mg/mL: and bis-tris buffer 83 mmol/L, pH 6.0. The films were spread with a GARDCO spreader at 250 microns wet thickness, and the time of exposure of blood specimens to dried reagent films was 10 sec. The absorbance at 650 nm after 20 sec. additional incubation was measured on a Hitachi U-2000, using a custom-designed optical assembly in which an incident light beam (1 mm aperture) crosses the reaction capillary perpendicularly to the mounted strip and co-axially with the center of the reaction capillary. It is important to note that absorbance responds generally linearly to glucose concentration.

FIGS. 11a–11c comprise three comparative Hematocrit interferograms for experimental results that compare the present invention (labeled as "MICRONIX") (FIG. 11a) with two field methods for whole blood glucose the Fasttake (sensimetric) FIG. 11b and Accucheck (photometric) meters, FIG. 11c. Specimens with varying hematocrit levels were constructed from one (1) blood draw, by aliquotting serum from slow centrifugation supernates among test specimens then and resuspending the cells. The levels shown were verified by capillary hematocrit measurements made with (CRITOCAPS™, which is a product of Oxford Labware). Measured "apparent" glucose concentrations from normal and spiked series (100 and 250 mg/dL respectively) were plotted against hematocrit. The film/reagent films and modes of measurement for the test are the same as described in connection with FIG. 10.

Figure 12A:
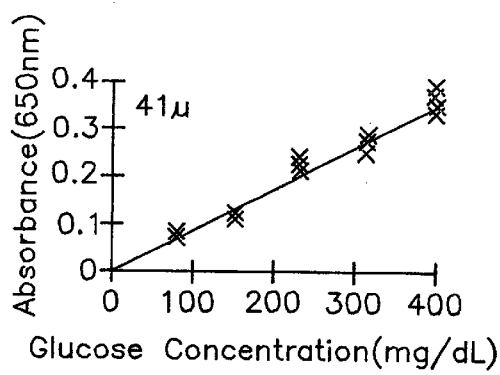
FIGS. 12a, 12b, 12c and 12d illustrate an experiment demonstrating relative independence of photometric signals from the depth of the blood layer flowing through the collection capillary and over the reagent film of the device.
Figure 12B:
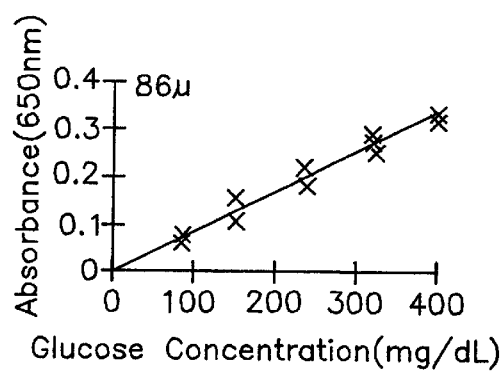
Figure 12C:
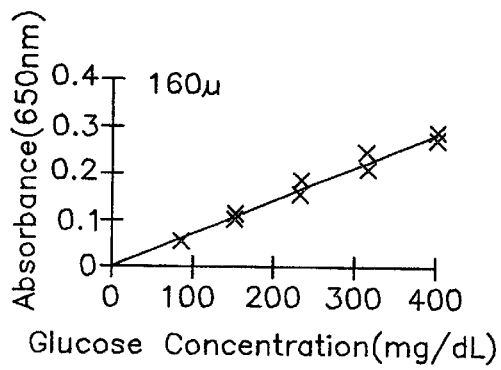
Figure 12D:
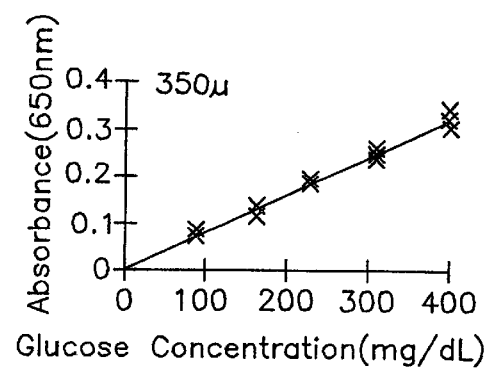

FIGS. 12a–12d illustrate the experimental results achieved from experiments where the measured absorbance was determined as a function of glucose concentration (mg/dh) wherein using the present invention, the factor varied among the graphs was the thickness levels of the blood reservoir bed. The thickness of the blood reservoir bed was determined by subtracting the thickness of the divided reagent film from the thickness of the reaction capillary. FIG. 12a illustrates this for a 41$\mu$ reservoir bed thickness level; FIG. 12b for a 86 $\mu$ reservoir bed thickness level; FIG. 12c for a 160 $\mu$ reservoir bed thickness level; and FIG. 12d illustrates the absorbance at 650 nm for a 350 $\mu$ reservoir bed thickness level.

That thickness was modulated using a double adhesive tape punch out/laminating technique, with fine tuning of thicknesses being achieved by spreading out "spacer" polymer films and measuring the thickness levels of dried films with a dial/digital readout micrometer. Reagent concentrations in UCAR 462 films and the time of sample exposure are calculated to those discussed in connection with FIG. 10.

Supportive Mechanisms

Support for buildup of a gradient of capillary force might also be provided chemically by inclusion in polymer/reagent mixtures of surface active substances. Surfactants are often included in clinical reagents for lowering surface tension in order to accelerate reaction kinetics. In the proposed capillary designs, the chemical reagents, together with suitable surfactants are encapsulated within the reagent film and thus only marginally dissolved by blood as it moves down the capillary channel. The result is a gradient of surfactant concentration and surface tension, the first decreasing, the second increasing in a downstream direction. Since capillary force is positively correlated with surface tension, the gradient in capillary force between collection capillary and wicking component can be augmented by inclusion in the reagent film of appropriately selected surface active substances.

Several design features of the device can advantageously be exploited for signal engineering and dosing. Sensitivity could be maximized by: coating both interior walls of the collection capillary with reagent film; increasing the thickness of the reagent film(s); increasing the time period of incubation by reducing the speed of capillary pull-through via variations in capillary dimensions; increasing the distance between reagent film surface(s) and opposing capillary wall(s), i.e. the thickness (height) of the layer of the collection capillary occupied by blood ("reservoir"). Dosing can be engineered via variations of interior capillary dimensions.

Features

The exemplary test strip devices of the present invention have several principal novel features:

1) Because red cells do not adhere to the reagent film when blood is pulled through the capillary channel, the device does not require a discrete plasma separating member for filtering out the red cells;

2) Owing to the laminar flow of a layer of blood over the reagent film, a blood spreading layer, as required in most other current test strips, is also not needed; these two features make the method minimally invasive as less than one (1) $\mu$L of whole blood is needed to carry out an analysis; they also reduce manufacturing complexity and cost;

3) Since cellular component is continually removed from the test field surface, the cells are inhibited from clogging or temporarily covering the test field surface; this "mobile sample" feature renders the device less dependent on the volume of cellular component, notably hematocrit;

4) Interference by hemolysis is not an issue because potentially hemolysis inducing filtering or absorbent materials are not needed;

5) In the case of transparency of both reagent film and collection capillary, linear optical signals can be acquired from transmittance measurements. Linear signal recognition simplifies calibration procedures, meter design and cost. In contrast, all present instrumented colorimetric test strips measure reflectance, relying on a standard curve that is a) non-linear at all concentrations, and b) based on an inverse relationship between concentration and reflectance. The mathematical (Kubelka-Munk) relationship between reflectance and concentration, and the coefficients of the standard curve must therefore be constructed by the manufacturer prior to storage of the curve on a microchip built into the metering device. Since the curves are rarely identical for any given production lot of test strips, manufacturers usually provide calibration chips with each new lot of test strips. It is then the responsibility of users to update calibration by inserting the new chips into their meters. These methods are highly complex as they require complicated curve fitting and corrective factoring mathematics.

6) Method endpoints can be determined instrumentally as well as visually, enabling visual backup checks on instrumented measurements. For visual evaluation, a printed color chart can be provided with the test strip package.

7) A somewhat surprising feature of the invention is that enzymes and other molecules encapsulated in the candidate polymeric films are apparently not transported downstream as blood rehydrates the films and moves downstream through the capillary. This can be concluded from repeated findings that post-reaction color is uniform over the entire surface of reacted test fields.

8) A critical issue is specimen dosing, that is whether a test sample of appropriate size has been applied to the strip in order to obtain an accurate reading. With the exemplary test strip devices of the present invention, accurate sampling is "method-intrinsic": the user can actually see how the blood enters the entry capillary and how the collection capillary is filled with blood and then emptied (See, FIG. 9). Under-sampling and over-sampling is a lingering problem with current glucose test strip products. Over-sampling is particularly hazardous as it can lead to life-threatening insulin over-administration in response to an erroneously high glucose reading.

Applications

While the most obvious field of application for the technology may be in the rapid nano-analysis of constituents of blood, many other uses in fields where an analysis fluid contains particulate matter, e.g. cell and tissue cultures, particle suspensions, environmental and industrial samples, etc. are conceivable. Furthermore, the technology is by no means restricted to diagnostic test strips embodying reagent-containing polymeric films. In one comparatively simple application, the test strips 10, 50 could be exploited for obtaining a defined amount of particle-free analysis fluid. Examples may be blood plasma from whole blood, or cellular secretions from hybridomas or DNA expression vectors. In applications of this type, polymers used to implement films 29 would not have to contain detection reagents, but would only serve as absorbent media for isolation of particle-free analysis fluid. The fluids could be analyzed for components of interest in situ, or the polymer could be dried, and specimens transferred for analysis at distant specialized laboratories. One example may be in the evaluation of genetic disease in neonates for acquisition of nano-specimens of blood plasma, followed by transfer of the dried specimens to a specialized laboratory for analysis of plasma components by mass spectroscopy. Another example may be in providing miniature specimens for analysis of nucleotide probes by the polymerase chain reaction (PCR) method.

Manufacturing

Several manufacturing processes, all well known to those skilled in the art can be applied for definition of the collection component 20 and wicking component 22, 52 extending within the test strip devices 10, 50. Preferably, a first plate template and a second plate template are fused together during production to form a template of multiple units of finished product. A continuous strip of reagent film 29 may be dispersed on at least one of the two templates. The reagent films 29 are preferably dispersed with the aid of commercially available spreading machines. The thickness of the wet, freshly cast reagent films 29 is in the range between 50 and 500 microns (2–20 mil). Alternatively, members of reagent film 29 can be cast individually by any of several known dispensing techniques. Other methods for dispensing the reagent films 29 are screen or inkjet printing, spraying by means of an airbrush technique, or conventional dispensing of discrete quantities using a positive displacement micro-volume dispenser. After drying the reagent films 29 by stationary or forced air, they can be cut to any desired size for use in a test tab device 10, 50.

Definition of the collection component 20 and the wicking component 22, 52 can be accomplished by a punch-out and laminating technique, by embossing, heat stamping, or by flow injection or compression molding. Injection or compression molding are preferred because they are the most flexible and most precise (1$\mu$ tolerance) techniques with respect to providing any desired size or shape to the first plate 16 and the second plate 18. Such flexibility is important for optimization of flow dynamics throughout the interior capillary spaces of the collection component 20 and wicking component 52. The fusion of first plate 16 and the second plate 18 can be achieved by double adhesive tape, adhesive bonding, ultrasonic welding, or preferably by a mechanical snap-in technique. In this fashion, a manufacturing process can be engineered capable of producing continuous templates or sheets of finished product. Individual test strips 10, 50 are then die-cut from these templates.

The proposed manufacturing process is novel and advantageous. Current manufacturing technology for diagnostic test strips is based on lamination and adhesive or ultrasonic welding techniques applied to long continuous templates of solid support stock. These methods are bulky, space consuming and fraught with alignment imprecisions. They require large machines equipped with sophisticated donor-to-receiving roll alignment mechanisms and extensive operating electronics. Typically, these machines have cost tags in the multimillion dollar range and are dubious investments because the machines become dinosaurs with every transition to a new technology/product generation.

In contrast, injection molding is product unit focused, rapid, volume flexible, more precise, and more cost effective. One injection tool lasts for years and can produce millions of unit product. Because injection molding is a highly developed and mature technology, manufacturing could be performed by one of many competent companies. The cost efficiency of an injection molding manufacturing process is believed to be an appropriate response to the enormous cost pressures expected for the SMBG market stemming from both managed care and rapidly expanding prevalence.

In test strip embodiment 10 using absorbent material 12, a continuous strip of absorbent material is mounted adjacent to and coparallel with the continuous strip of reagent film so that after die-cutting of unit test strips, each individual reagent film member is in communicative fluid contact with its adjacent wicker member.

The test strip device 50 embodiment in which the wicking component 52 is a wicking capillary 62 can be manufactured in an analogous manner, essentially making the space otherwise occupied by the absorbent material 12 the wicking capillary 62. However, the space constituting the wicking capillary 62 has a surface/volume ratio significantly exceeding the surface/volume ratio of the collection component 20. This differential in surface/volume ratio (gradient of capillary force) becomes the main driver for the downstream flow of analysis fluid through the capillary space as capillary pull force in the downstream direction is a resultant function of the larger capillary active interior surface of the wicking capillary 62. Expansion of the interior surface of the wicking capillary 62 can be accomplished by a large variety of designs. The simplest of these would result from a compression of the height (thickness) dimension of the wicking capillary and an expansion of its width and/or length dimension.

A modification of this design that is believed to be advantageous is to divide the wicking capillary space into a plurality of contributory capillaries extending downstream from the collection capillary as shown in FIG. 5. By further increasing surface/volume ratio, a design of this type enhances volume pull-through per unit of time, permitting rapid test field exposure and early acquisition of reaction kinetic data. The production of a wicking capillary 62 (FIG. 2) featuring at least one restricted spatial dimension can be accomplished by a variety of designs. Either the height or the width dimension of a wicking capillary 62 (FIG. 2) or plurality of wicking capillaries 74, as shown in FIG. 5, can be restricted. From a product development and manufacturing standpoint, it is advantageous to restrict the interior height dimension of the capillary space in the downstream direction. Restriction of the height dimension can either be in a single height transition step (FIG. 2), in multiple steps (FIG. 6) or it can be continuous (FIG. 7).

It will be appreciated by those skilled in the art that the range of potentially functional designs for the interior capillary space is essentially unlimited. The sole unifying principle is that capillary force acting in the downstream direction is larger than capillary force acting in the upstream direction. This can be accomplished by a large variety of capillary architectures, including variations in shape, diameter, location, etc. Generally, capillary force acting in the downstream direction and hence the speed of emptying of the collection capillary increases as the number of wicking capillaries 74 increases and their inside diameters decrease. The principle is most profoundly expressed when the wicking component is a separate porous polymeric material (sponge).

EXAMPLES

The reasons why red cells can be removed from reagent films 29 with some, but by no means all types of transparent film materials are incompletely understood. We have tested a large number of polymeric film-forming materials, including both homogeneous polymer solutions as well as heterogeneous particle (latex) dispersions (Table 1). Acceptance/rejection criteria for performance are 1) clarity before and after addition of all reactive and non-reactive components, 2) smoothness and uniformity of film surface after spreading and after drying, 3) absence of red cell adherence to test fields after sampling and wicking, 4) clarity post-reaction, i.e. absence of or minimal rehydration opalescence, 5) uniformity of reaction color over entire test field, 6) depth of signal-to-concentration response (i.e. sensitivity), 7) proportionality of dose response (i.e. linearity), and 8) clarity and stability of reaction color.

Based on these criteria, several commercially available products were identified that displayed the desired properties (Table 2). To the applicant's knowledge, none of these materials have ever been previously investigated for use as plasma absorbing translucent reagent carriers in test strips not requiring integration of a cell/plasma separating material.

TABLE 2

TESTED AND FUNCTIONAL FILM POLYMERS

| FILM CHARACTERISTICS | FILM-FORMING POLYMERS |
|---|---|
| Water-soluble, natural | gelatin (type A, porcine skin, Sigma). |
| Water-soluble, synthetic | poly(N-vinyl pyrrolidone) K-90 (ISP Technologies) |
| Water-insoluble but swellable | poly(2-hydroxyethyl) methacrylate (Sigma) |
| Water-insoluble/ dispersions | urethane/methylpyrrolidone hybrid (Hybridur 570, Air Products); vinyl acetate/butyl acrylic copolymer (UCAR-357, Union Carbide); styrene/acrylic (UCAR-462, Union Carbide); vinyl acetate/acrylic (Flexbond 325, Air Products); vinyl acetate/ethylene copolymer (Airflex 400 H, Air Products); vinylacrylate copolymer (VIACRYL VSC 6295, Vianova Resins); vinylacrylate copolymer (VIACRYL VSC 6279, Vianova Resins). |

To demonstrate functionality and linear response, handmade teststrip devices 50 (FIG. 2) were prepared employing a double adhesive tape punchout/laminating technique. The material used for the film 29 was styrene/acrylic (UCAR-462, Union Carbide) cast onto sections of polycarbonate sheets. The films 29 contained a glucose oxidase/peroxidase/TMB reagent. A glucose concentration series of blood specimens was assayed by the experimental teststrip devices 50. As expected from absorbance measurement, the experiment demonstrated linear signal-to-concentration responses as illustrated in FIG. 10.

A much appreciated phenomenon, known from commercial teststrips for blood glucose is hematocrit dependence (i.e. dependence upon the volume portion of blood occupied by red blood cells). Most current glucose systems produce results that are inversely correlated with hematocrit. In the case of photometric teststrips (all of which are believed to employ a blood separating member), excess red cells block diffusion of plasma and hence glucose into the detection member of a device. In the case of sensor strips (which measure whole blood instead of separated plasma), a separating member is not required, but the plasma is "diluted" with excess red cells at high hematocrit levels. In either case, results will be erroneously low. Conversely, at below normal hematocrit, more glucose reaches the detection site, causing results to be falsely high.

In the method of the proposed device, hematocrit dependence is substantially reduced, as concluded from interferogram plots performed on experimental Micronix test strips 50 and two field methods for blood glucose from two different major companies, one of the methods being photometric, the other sensimetric. The plots reveal massive positive biases for the field methods at low hematocrit, and a much stronger decline of apparent glucose concentrations with increasing hematocrit, as shown by regression slopes of FIG. 11. It is hypothesized that lack of significant hematocrit interference with the Micronix method is the result of supplying the blood to comparatively thin reagent films 29 as a uniform "mobile sheet", thereby continually removing cells by capillary force as the blood moves downstream through the collection capillary 24. In this fashion, uniform and complete film rehydration may be facilitated.

The candidate reagent film rehydration technology, in concert with focused blood delivery to the test strip detection site, enabled by spatially defined capillary microelements, opens up an astonishing potential for device miniaturization and hence minimal invasiveness. This is evidenced by a recent experiment in our laboratory in which we incrementally challenged the thickness (height) dimension of the collection capillary 24. The experiment shows that signal intensity does not diminish down to a level as low as $40\mu$ (See, FIG. 10), and possibly lower than that. Since the diameter of the collection capillary 24 was 3 mm, the volume of blood inside the cylindrical collection capillary 24 ($r^2\pi h$) at that thickness is only $1.5^2$ 3.14 0.04)=283 nanoliter, less than one hundredth ($\frac{1}{100}^{th}$) the volume of a drop of blood.

All that is required for the candidate thin film technology to work is a 5–7 mm² polymeric reagent film (dry thickness approx. 50 microns) cast inside an injection-molded capillary channel. This feature of the technology enables an extreme degree of simplicity, speed, and miniaturization of analytical elements, to a level we believe no other current technology comes close to.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected.

Figure 8:
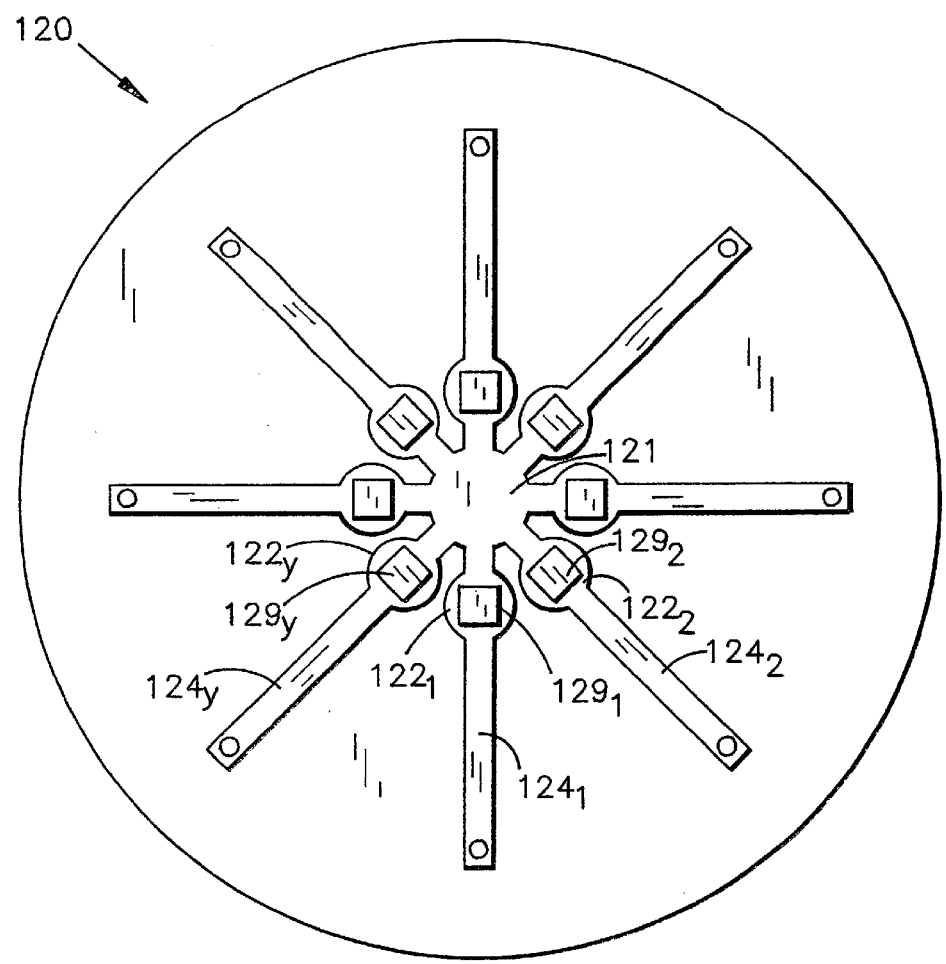
FIG. 8 illustrates a top view of a multiple test cassette that permits analysis of 8 separate analytes.

For example, one could envision an emergency medicine or stat-lab clinical analyzer capable of instantly performing a complete toxic or metabolic profile. An entire eight to twelve parameter panel could be performed on about one half (½) drop of blood, without centrifugation or any other form of sample or reagent manipulation. As depicted in FIG. 8, a multi-analyte test strip device or multiple test cassette 120 could be injection-molded, being comprised of an application port 121, a plurality of collection components $122_1, 122_2, \ldots 122_Y$ coupled to the application port, and a plurality of wicking components $124_1, 124_2, \ldots 124_Y$ coupled to the collection components $122_1, 122_2, \ldots 122_Y$. In particular, each of the plurality of collection components includes a single reagent film $129_1, 129_2, \ldots 129_Y$ for a different analyte. The optical alignment could be composed by not much more than a pair of pea-sized photo diodes, and data could be processed by a microprocessor chip the size of a postage stamp. Alignment of any given test field with the optical path could be accomplished by either moving the photo diodes or the multiple test cassette 120 via a robotic x/y axial assembly. Alternatively, the test fields could be lined up in sequence for stepwise advancement into the optical path.

What is claimed is:

1. A test strip device for testing a fluid containing an analyte, comprising a collection component comprising an inlet, a collection capillary structured to draw said fluid into said collection component via said inlet by exerting capillary forces upon said fluid applied to said inlet, and a film operable to collect said analyte from said fluid as said fluid is drawn over said film; and a wicking component coupled to said collection component and structured to draw said fluid over said film and into said wicking component by exerting capillary forces on the fluid, whereby the wicking component, without the aid of a filtration device, exerts sufficient capillary forces on the fluid to effectively sweep said film free of particulate matter contained in said fluid.

2. A test strip device for testing a fluid containing an analyte, comprising: a collection component comprising an inlet, a collection capillary structured to draw said fluid into said collection component via said inlet by exerting capillary forces upon said fluid applied to said inlet, and a film operable to collect said analyte from said fluid as said fluid is drawn over said film; and a wicking component coupled to said collection component and structured to draw said fluid over said film and into said wicking component, whereby the wicking component exerts sufficient capillary forces on the fluid to effectively sweep said film free of particulate matter of said fluid, without employing filtration materials.

3. The test strip device of claim 2, wherein said fluid is whole blood and said particulate matter comprises cellular matter contained in said blood.

4. The test strip device of claim 2, wherein said wicking component comprises absorbent material positioned to draw said fluid from said film and into said wicking component.

5. The test strip device of claim 2, wherein said wicking component comprises a wicking capillary structured to draw said fluid from said collection component and into said wicking component and whereby the wicking component exerts sufficient capillary forces on the fluid to effectively sweep said film free of particulate matter of said fluid, without employing filtration or other mechanical removal materials.

6. The test strip device of claim 5, wherein the capillary force exerted on said fluid by said wicking component is greater than the force exerted on said fluid by the collection component.

7. The test strip device of claim 5, wherein said wicking component has a greater surface-to-volume ratio than said collection component in order to induce a gradient of capillary force upon said fluid, the gradient facilitating fluid transport from the collection component to the wicking component.

8. The test strip device of claim 2, wherein said wicking component comprises a plurality of wicking capillaries structured to draw said fluid from said collection component and into said wicking component.

9. The test strip device of claim 2, wherein said film absorbs said analyte as said fluid flows over said film.

10. The test strip device of claim 2, wherein said film comprises at least one water soluble polymer.

11. The test strip device of claim 2, wherein said film comprises at least one water insoluble polymer.

12. The test strip device of claim 2, wherein said film is selected from the group consisting of vinylacrylate polymer, ether acrylate polymer, vinylacrylate copolymer and ether acrylate copolymer, urethane/methylpyrolidone hybrid polymer, and vinylacetate.

13. The test strip device of claim 2, wherein said film is transparent and comprises at least one reagent that reacts with said analyte to produce a product suitable for analyzing said analyte with transmittance photometry.

14. The test strip device of claim 13, wherein said product produced by said at least one reagent and said analyte causes said transmittance photometry to generate a signal that is substantially proportional to analyte concentration.

15. The test strip device of claim 2, wherein said film is opaque and comprises at least one reagent that reacts with said analyte to produce a product suitable for analyzing said analyte with reflectance photometry.

16. The test strip device of claim 2, wherein said film comprises at least one reagent that reacts with said analyte to produce a product suitable for analyzing said analyte with fluorimetry.

17. The test strip device of claim 2, wherein said film comprises at least one reagent that reacts with said analyte to produce a product suitable for analyzing said analyte with luminescence photometry.

18. A test strip device for testing a fluid containing an analyte, comprising:

a collection component comprising an inlet, a collection capillary structured to draw said fluid into said collection component via said inlet by exerting capillary forces upon said fluid applied to said inlet, and a film operable to collect said analyte from said fluid as said fluid is drawn over said film; and a wicking component coupled to said collection component and structured to draw said fluid over said film and into said wicking component by exerting capillary forces on the analyte fluid, wherein said collection component and said wicking component are collectively structured with a particular dimension that progressively decreases cross sectional area from said inlet to said wicking component in order to facilitate a general increase in capillary force exerted upon said fluid as said fluid flows from said inlet to said wicking component, whereby the wicking component without the aid of a filtration device exerts sufficient capillary forces on the fluid to effectively sweep said film free of particulate matter contained in said fluid.

19. The test strip device of claim 18 wherein said collection component and said wicking component are collectively structured having at least two transition steps in a particular dimension in order to facilitate a general increase in capillary force exerted upon said fluid as said fluid flows from said inlet to said wicking component.

20. The test strip device of claim 18, wherein said wicking capillary comprises a venting channel operable to relieve pressure within said wicking capillary as said wicking capillary fills with said fluid, and the cross sectional area decreases in a generally continuous manner from said inlet to said wicking component to thereby generally continuously increase the surface to volume ratio of the collection component.

21. A test strip device for testing blood glucose levels, comprising a first translucent plate coupled to a second translucent plate that collectively include:

a collection component comprising
  an entry capillary comprising an inlet and an entry vessel that are structured to exert capillary forces on whole blood applied to said inlet in order to draw said whole blood into said entry vessel,
  a collection capillary comprising a collection inlet coupled to said entry vessel and a collection vessel that are structured to draw blood from said entry capillary into said collection vessel by exerting capillary forces on said whole blood in said entry vessel, and a translucent reagent film on at least one wall of said collection capillary, said translucent reagent film comprising a glucose oxidase reagent that reacts with glucose in said whole blood as said glucose diffuses into said translucent reagent film; and a wicking capillary comprising a wicking inlet coupled to said collection vessel and a wicking vessel that are structured to effectively sweep said translucent reagent film free of red blood cells as said whole blood is drawn over said film and into said wicking vessel, without filtration materials.

22. The test strip device of claim 21, wherein said collection component and said wicking capillary are collectively structured with at least two transition steps in a particular dimension in order to facilitate a general increase in capillary force exerted upon said whole blood as said whole blood is drawn from said inlet of said collection component into said wicking vessel.

23. The test strip device of claim 22, wherein said wicking capillary comprises a venting channel toward an end of said wicking vessel that is distal from said wicking inlet, said venting channel operable to relieve pressure within said wicking capillary as said wicking capillary fills with said whole blood.

24. The test strip device of claim 23, wherein said collection component and said wicking capillary are collectively structured with a particular dimension that decreases in a generally continuous manner from said inlet to said venting channel in order to facilitate a general increase in capillary force exerted upon said whole blood as said whole blood is drawn from said inlet toward said venting channel of said wicking capillary.

* * * * *